(12) United States Patent
Gross et al.

(10) Patent No.: US 6,317,630 B1
(45) Date of Patent: Nov. 13, 2001

(54) DRUG DELIVERY DEVICE

(76) Inventors: Yossi Gross, 82 Seafield Road, Dublin 3 (IE); Zvika Nitzan, 37 Brande Street, Petah-Tikva (IL), 49600

( * ) Notice: Subject to any disclaimer, the term of this patent is extended or adjusted under 35 U.S.C. 154(b) by 0 days.

(21) Appl. No.: 09/239,934

(22) Filed: Jan. 29, 1999

(51) Int. Cl.[7] .............................. A61N 1/30; A61N 1/00
(52) U.S. Cl. .............................................. 604/20; 607/154
(58) Field of Search ............................ 604/20, 19, 502; 128/898; 607/3, 50, 115, 152, 153, 154; 606/32

(56) References Cited

U.S. PATENT DOCUMENTS

| | | | |
|---|---|---|---|
| 3,915,151 | * 10/1975 | Kraus | 128/1.5 |
| 4,312,340 | 1/1982 | Donadelli | 128/207.21 |
| 4,313,438 | 2/1982 | Greatbatch | 128/207.21 |
| 4,314,554 | 2/1982 | Greatbatch | 128/207.21 |
| 4,403,618 | * 9/1983 | Turner et al. | 128/804 |
| 4,471,787 | 9/1984 | Bentall | 128/804 |
| 4,556,051 | * 12/1985 | Maurer | 128/1.5 |
| 4,611,599 | 9/1986 | Bentall et al. | 128/422 |
| 4,787,888 | * 11/1988 | Fox | 604/20 |
| 4,820,263 | 4/1989 | Spevak et al. | 604/20 |
| 4,926,881 | 5/1990 | Ichinomiya et al. | 128/804 |
| 4,942,884 | * 7/1990 | Ichinomiya et al. | 128/804 |
| 5,019,034 | 5/1991 | Weaver et al. | 604/20 |
| 5,190,761 | 3/1993 | Liburdy | 424/450 |
| 5,312,325 | 5/1994 | Sibalis | 604/20 |
| 5,328,454 | 7/1994 | Sibalis | 604/20 |
| 5,336,168 | 8/1994 | Sibalis | 604/20 |
| 5,372,579 | 12/1994 | Sibalis | 604/20 |
| 5,400,041 | 3/1995 | Strickland | 343/700 |
| 5,405,614 | 4/1995 | D'Angelo et al. | 424/449 |
| 5,458,569 | 10/1995 | Kirk, III et al. | 604/20 |
| 5,474,527 | 12/1995 | Bettinger | 604/19 |
| 5,507,790 | 4/1996 | Weiss | 607/100 |
| 5,551,953 | * 9/1996 | Lattin et al. | 604/20 |
| 5,569,166 | * 10/1996 | Stone | 601/21 |
| 5,578,065 | * 11/1996 | Hattori et al. | 607/46 |
| 5,598,168 | 1/1997 | Evans et al. | 343/700 |
| 5,618,284 | 4/1997 | Sand | 606/5 |
| 5,678,202 | 10/1997 | Filimon et al. | 455/89 |
| 5,688,232 | 11/1997 | Flower | 604/20 |
| 5,697,951 | 12/1997 | Harpstead et al. | 607/3 |
| 5,741,317 | 4/1998 | Ostrow | 607/85 |
| 5,766,232 | 6/1998 | Grevious et al. | 607/60 |
| 5,766,249 | 6/1998 | Griffith | 623/12 |
| 5,888,185 | * 3/1999 | Regan | 600/15 |
| 5,911,223 | * 6/1999 | Weaver et al. | 128/898 |
| 5,978,701 | * 11/1999 | Johnson et al. | 604/20 |
| 6,018,678 | * 1/2000 | Mitragotri et al. | 604/20 |
| 6,041,253 | * 3/2000 | Kost et al. | 604/20 |
| 6,041,262 | * 3/2000 | Beder | 607/139 |
| 6,042,531 | * 3/2000 | Holcomb | 600/13 |

FOREIGN PATENT DOCUMENTS

| | | |
|---|---|---|
| 2 151 489 A | 7/1985 | (GB). |
| 2 240 720 A | 8/1991 | (GB). |
| WO 86/02846 | 5/1986 | (WO). |
| WO 94/13357 | 6/1994 | (WO). |
| WO 96/13302 | 5/1996 | (WO). |
| WO 97/11742 | 4/1997 | (WO). |
| WO 98/14235 | 4/1998 | (WO). |

* cited by examiner

*Primary Examiner*—Sharon Kennedy
(74) *Attorney, Agent, or Firm*—Hamilton, Brook, Smith & Reynolds, P.C.

(57) ABSTRACT

The present invention relates to a drug delivery device incorporating current and electromagnetic field sources to provide a controlled drug delivery system. The system can include a membrane with an RF antenna, a plurality of electrodes and contacts to provide an interface to a controller housing.

48 Claims, 8 Drawing Sheets

DRUG DELIVERY DEVICE

BACKGROUND OF THE INVENTION

Medical and cosmetic preparations whose molecules are too large to be easily accommodated by skin pores are not efficacious in topical application. Various methods for increasing the efficacy of these preparations in topical application are known. One such method is the iontophoretic process.

Iontophoresis is the migration of ions when an electric current is passed through a solution containing the ions, usually the ionic form of a drug or therapeutic agent. Iontophoresis can provide the non-invasive transdermal delivery of ionized drugs to a patient by applying a current to a patch placed on a patient's skin. The current forces the medication, located in the patch or on the patient, to enter the patient's bloodstream through the skin.

Electromagnetic energy in the radio frequency (RF) range has also been described as useful to aid in the healing of damaged tissue. Often, large systems including an antenna and an RF generator are positioned near tissue to be treated. Due to the size and cost of these systems, patients require scheduled appointments for treatment and positioniing of the wound or treatment area can be awkward and uncomfortable.

The application of an electromagnetic field to the body is also used to enhance vascular efficiency. Increased excitation of the vascular system is an important component to wound healing.

Iontophoresis is known to enhance drug delivery over passive transdermal delivery. In the treatment of cancerous tumors, it has been argued that a therapy of iontophoretic drug delivery and the separate application of electromagnetic energy results in either increased drug delivery to the targeted area or a decrease in the amount of drug needed to be delivered due to heightened efficiency of the delivery. These treatments must be delivered separately with existing systems.

A continuing need exists, however, for providing improvements to current methods for the transdermal delivery of medications.

SUMMARY OF THE INVENTION

The invention relates to a drug delivery device that can be used to deliver a current and electromagnetic energy to a site. The device call include a membrane having electrodes that deliver a current to a medication or preparation for transdermal delivery, an antenna for transmitting electromagnetic energy into the tissue underlying the membrane that can provide treatment of the tissue and/or enhance delivery of the medication, and a circuit that connects a control signal source to the antenna, and the electrodes.

This system solves problems associated with the prior art by providing a small portable device for the use of electromagnetic energy to aid in the delivery of medication. This has several advantages including increased blood circulation at the site and/or enlarging of pores in the skin thereby increasing the flow of medication. The present system thus provides a non-invasive method for adjusting physiologic, metabolic and growth behavior of cells and tissues. The electromagnetic signals call also be used to treat conditions such as pain and edema associated with soft tissue injuries.

In one embodiment of the invention, medication to be delivered to a patient is independent from the drug delivery device. For example, a medication can first be applied to a patient's skin and the drug delivery device then placed on the patient in contact with the medication. In another preferred embodiment, the medication is stored in a reservoir in the membrane or in the control housing prior to use of the drug delivery device. The removal of an adhesive backing to expose an adhesive on the membrane that secures the membrane to the patient can also expose medication on the membrane surface.

A control signal source is contained within a controller housing having surface contacts that match the interface contacts of the membrane. The controller housing can have an upper surface with one or more buttons to control operation of the membrane. The controller housing contains a battery to power the device, a microprocessor or integrated control circuit connected to an RF transmitter, and a current stabilizer circuit.

In one embodiment, the control signal source allows for the simultaneous application of the electromagnetic fields and current to a site. The control signal source can also allow for independent application of either the electromagnetic field or the current to a site or can allow for application of the electromagnetic field and the current in an alternating pattern. The drug delivery device provides a small, light weight, low power control signal source that can simultaneously, or in any selected sequence, deliver an iontophoretic treatment and/or an electromagnetic signal to a region of interest. Low power operation has provided an increase in the frequency range available for use.

In another embodiment, the control housing contains a selector which allows the user to manually select the target physiologic site and the type of drug to be delivered to the site from a programmed control sequence. Selecting for a specific drug and target tissue will change the characteristics of the electromagnetic field and current produced by the control signal source. In another embodiment, selection of a physiologic site or region of interest and the type of drug to be delivered from a programmed control sequence is done from a remote computer. The computer provides the control sequence to the control signal source by either a standard cable connection or a wireless transmission.

The membrane can be attached to the control housing by an adhesive, or by other electrical, magnetic or mechanical attachment methods. Separation of the membrane and the control housing provides for reuse of the control signal source with the membrane being disposable.

In another embodiment of the invention, the membrane and control signal source are integrated in a single unit such that the antenna and electrodes are directly connected to the control circuit. Depending upon the particular application, the entire unit can be disposable or it can be sterilized for further use.

The invention also relates to a method of using a drug delivery device. The method includes applying a medication to a patient, attaching a membrane containing an antenna for transmitting an electromagnetic field and electrodes for transmitting a current over the medication area, and connecting the antenna and the electrodes to a control signal source. The method further includes activating the control signal, applying the electromagnetic field and current to the medication area, and stimulating the medication to travel through the skin of the patient.

Figure 1:
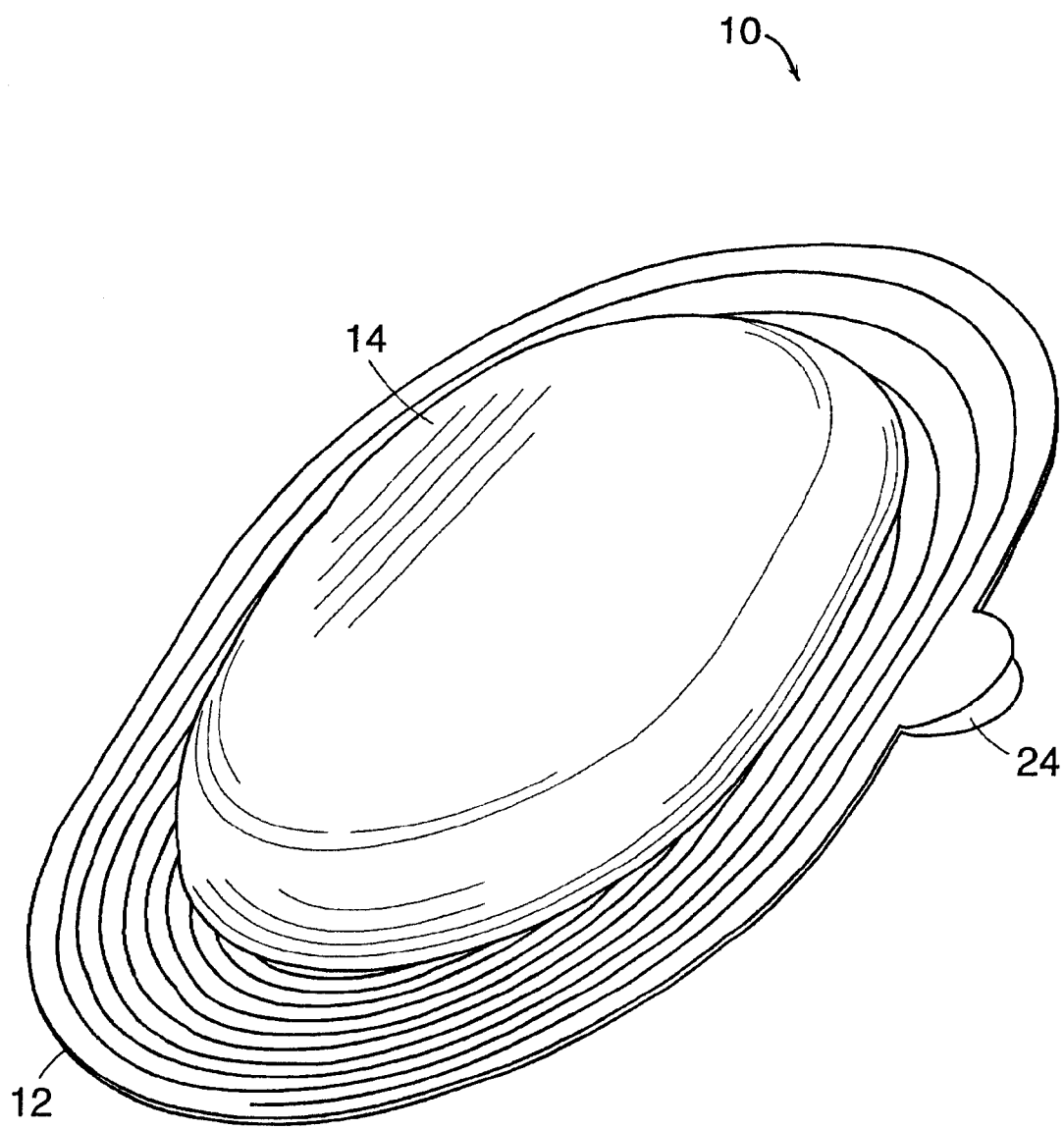
FIG. 1 illustrates a perspective view of a drug delivery device in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention is shown in FIG. 1. The invention, a drug delivery device 10, can comprise two primary components, including a membrane 12 and a control signal source 14. The membrane 12 and control signal source 14, in a preferred embodiment, are separate components which allows for disposal of the membrane 12 and sterilization of the control signal source 14 after use. In an alternate embodiment, the membrane 12 and control signal source 14 are integrated as a single unit. The drug delivery device 10 can be affixed to a patient's skin and used to deliver an iontophoretic preparation to the patient through that site. In one embodiment of the invention, an iontophoretic preparation can be applied to the site of interest and the drug delivery device 10 is then placed on the site over the area of application. In an alternate embodiment, the drug delivery device 10 can contain an iontophoretic preparation dispensing ultit, eliminating the need to apply the iontophoretic preparation on a patient's skin prior to placement of the membrane 12. The dispensing unit call comprise either an iontophoretic preparation layer or an iontophoretic preparation reservoir attached to or within the membrane, for example. A removal tab 24 can be included on the membrane 12 to facilitate efficient removal of the drug delivery device 10 at the conclusion of the process.

Figure 2:
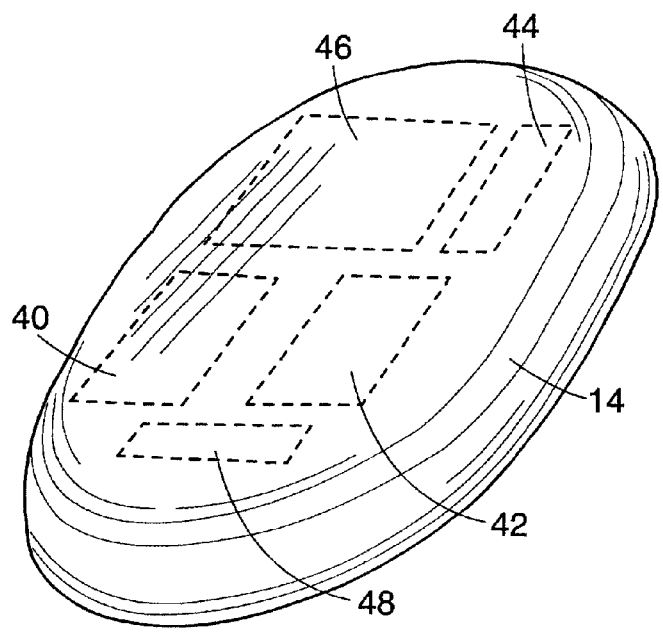
FIG. 2 shows a perspective top view of a control signal source for a drug delivery device.

An embodiment of a control signal source 14 for the drug delivery device 10 is shown in FIG. 2. The control signal source 14 delivers a signal to an antenna that transmits an electromagnetic field and also delivers a current directed through electrodes on the membrane 12. In a preferred embodiment, the current is used for iontophoresis. In one embodiment, the control signal source 14 allows for simultaneous application of the electromagnetic field and the iontophoresis current to a patient site. In another embodiment, the control signal source 14 transmits either the electromagnetic field or the current to a site independently. In another embodiment, the control signal source 14 allows for alternating or periodic application of the electromagnetic field and the current to a patient site. Thus, the control signal source 14 can selectively control transmission of the electromagnetic field and the current either simultaneously, independently, or in an alternating pattern, as previously described. Also, the current and electromagnetic duty cycles can be of the same length. In alternate embodiments, different lengths can be used.

In a preferred embodiment of the invention, the electromagnetic field controlled by the control signal source 14 is a radio frequency (RF) electromagnetic field. The RF electromagnetic field can have a frequency in the range of 10 MHZ and 3 GHz with a preferred frequency of 27 MHZ. The RF electromagnetic field can have a power level in the range of 10 mW and 1 W with a preferred power requirement of about 1 mW. In a preferred embodiment, the current transmitted by the control signal source 14 can have a current in the range of 50 uA to 4 mA, with a preferred current of about 1 mA. When the current and the RF electromagnetic pulses are synchronized, the phase shift between them can be selected within the range of 0 to 180 degrees.

The control signal source 14 can contain a microprocessor 48 which can be programmed by the user depending on several factors including the type of medication, the condition of the patient and the dosage required. The control signal source 14 can also contain a transmitter 42 which delivers an electromagnetic signal to the membrane 12. The control signal source 14 can also contain a power source 46. In a preferred embodiment, the power source 46 is a battery. In this embodiment, the battery can be rechargeable and reusable. Alternately, the control signal source 14 can be powered by an external power source. In another preferred embodiment, the control signal source 14 comprises a power switch 40. The power switch 40 prevents transmission of current to the membrane 12 when the membrane 12 is not attached to or has been detached from a patient's skin. The control signal source 14 can also contain a current stabilizer 44 which maintains the required current levels despite variations in the number of ions being transported.

Figure 3:
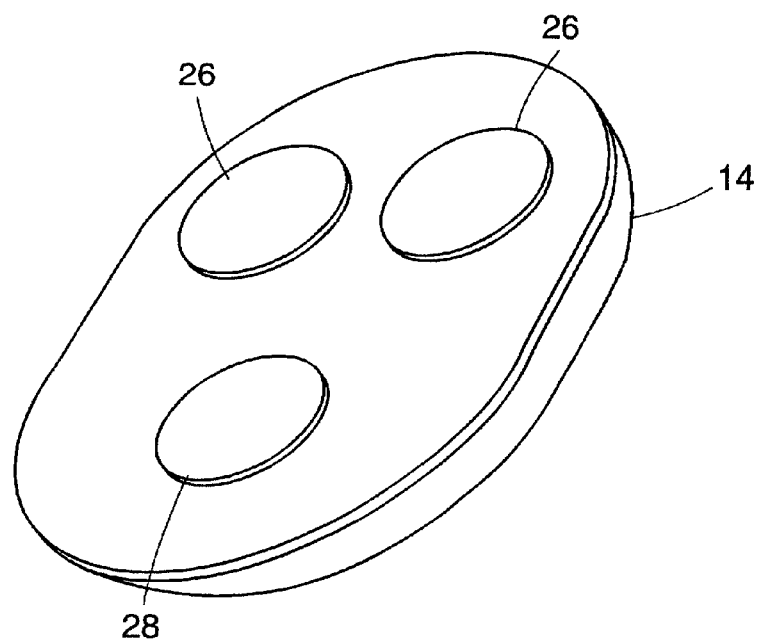
FIG. 3 shows a perspective bottom view of a control signal source for a drug delivery device.

FIG. 3 shows a bottom view of the control signal source 14 which contains electrode contacts 26 and an antenna contact 28. The electrode contacts 26 attach to the membrane 12 and allow current to pass to the membrane 12. Similarly, the antenna contact 28 attaches to the membrane 12 and allows transmission of an electromagnetic field to the membrane 12.

The drug delivery device 10 can be used to deliver different types of medications to different tissue sites on a patient. For example, the drug delivery device 10 can be used to deliver drugs to a patient undergoing bone treatment, wound treatment, or cancerous tumor treatment. The physiologic differences among these sites and the pharmacologic differences in the drugs used to treat the sites can require the control signal source 14 to produce an electromagnetic field and an current unique to each situation.

Figure 4:
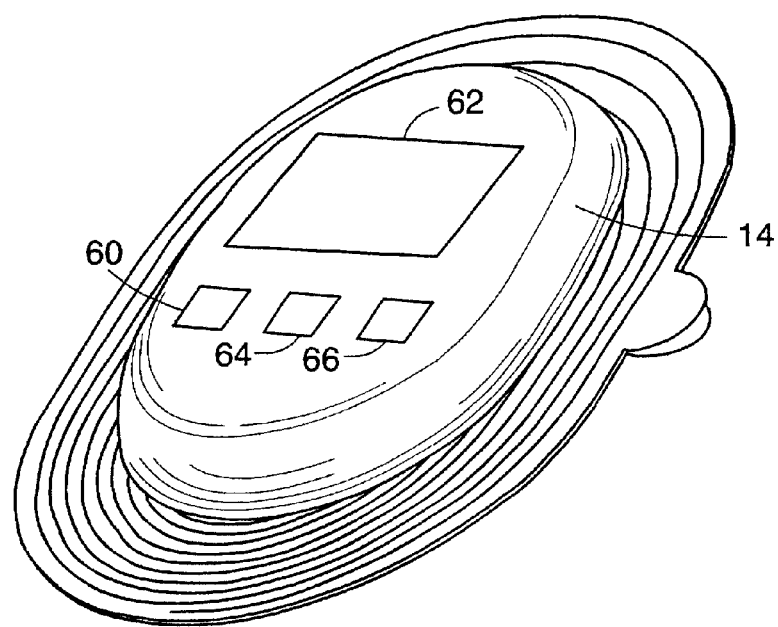
FIG. 4 illustrates a perspective view of an embodiment of the control signal source for the drug delivery device.

FIG. 4 shows an embodiment of the control signal source 14 for the drug delivery device. In one embodiment, the control signal source 14 can contain an on-off switch 60 which allows or prevents production of an electromagnetic field and a current by the control signal source 14. In this embodiment, the control signal source 14 can be used with a specific medication delivered in a specific type of tissue treatment. The user can manually toggle the switch 60 into an on or an off position. In an alternate embodiment, the control signal source 14 contains selector switches 64, 66 and a display 62. The selector switches 64, 66 allow the user to manually select the target physiologic site and the type of drug to be delivered to the site. This will change the characteristics of the electromagnetic field and current produced by the control signal source 14. The selector switches 64, 66 allow the user to scroll through preprogrammed choices of possible target physiological sites and medication types, viewed on the display 62, in order to choose the proper site and drug needed for their treatment. In one embodiment, the display 62 is a liquid crystal display. In a preferred embodiment, the control signal source 14 contains the on-off switch 60, the selector switches 64, 66, and the display 62 on one unit, as shown in FIG. 4.

Figure 5:
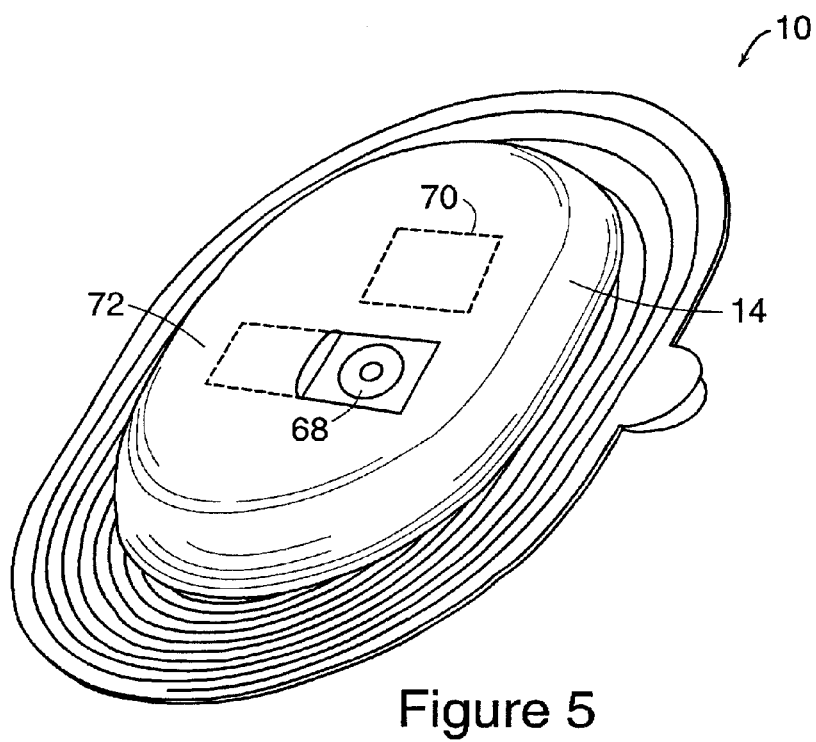
FIG. 5 illustrates a perspective view of an alternate embodiment of the control signal source for the drug delivery device.

FIG. 5 shows an alternate embodiment of the control signal source 14 for the drug delivery device 10. In one embodiment, the control signal source 14 can contain an input port 68 which allows the physical connection of the control signal source 14 to an external computer. Connection to a computer allows the control signal source 14 to receive, in electronic form, a programmed control sequence unique to a particular medication and tissue site combination. The programmed control sequence can set the parameters for the electromagnetic field and current produced by the control signal source 14. The input port can comprise a door 72. The door 72 can be used to expose the port 68 in order to provide connection to a computer. The door 72 can also be used to seal the port 68 and prevent exposure to any possible contaminants. In an alternate embodiment, the control signal source 14 comprises a wireless receiver 70 which allows the control signal source 14 to receive, in electronic form, a programmed control sequence unique to a particular medication and tissue site combination without physical connection to a computer. The wireless receiver 70 can receive data from an external computer by means of a wireless transmitter connected to the computer. In a preferred embodiment, the control signal source 14 contains both an input port 68 and a wireless receiver 70 which allows the user the flexibility of choosing the method for receiving programmed control sequence data.

Figure 6:
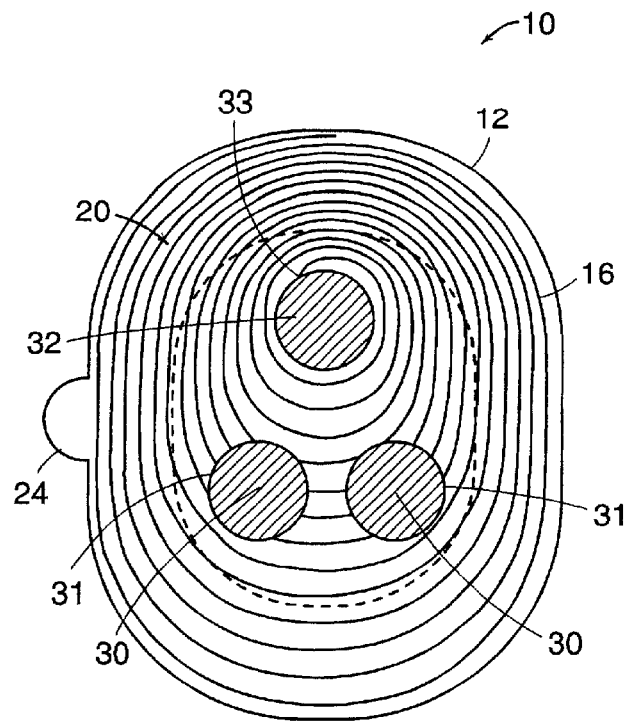
FIG. 6 illustrates a top view of a membrane for drug delivery device.

FIG. 6 shows a top view of the membrane 12 of the drug delivery device 10. The membrane 12 can be a patch made from a paper material, plastic, or other flexible material. Moreover, the material can be coated with other material such as polyethylene. In one embodiment, the paper material has a thickness ranging between 0.1 mm and 0.5 mm with a preferred thickness of about 0.3 mm. The membrane can have a surface area in the range of 5 $cm^2$ to 200 $cm^2$.

The top surface 20 of the membrane 12 comprises, in a preferred embodiment, adhesive 30 for the electrode contacts 31, an adhesive 32 for the antenna contact 33, and an antenna 16. The adhesives 30 for the electrode contacts 31 and the adhesive 32 for the antenna contact are located on the membrane electrode contacts 31 and antenna contact 33, respectively, These adhesives attach the membrane electrode contacts 31 and antenna contact 33 to the electrode contacts 26 and an antenna contact 28 on the control signal source 14. The adhesives 30, 32 are conductive adhesives and provide sufficient coupling, both electrical and mechanical, between the membrane 12 and the control signal source 14.

The membrane 12 comprises an antenna 16 which distributes an electromagnetic field transmitted by the control signal source 14. In one embodiment, the antenna 16 is printed on the membrane 12. In another embodiment, the antenna 16 is printed on the top surface 20 of the membrane 12. The antenna 16 can be printed on the membrane 12 to form a spiral pattern. The spiral pattern allows for an efficient distribution of the electromagnetic field to a patient's skin. When the drug delivery device 10 is placed on a patient, the proximity of the antenna to the patient's dermis can be in the range of 0.1 mm to 1.0 mm with a preferred proximity of 0.4 mm. This proximity of the antenna to the skin reduces the power requirements necessary to produce the electromagnetic field.

Figure 7:
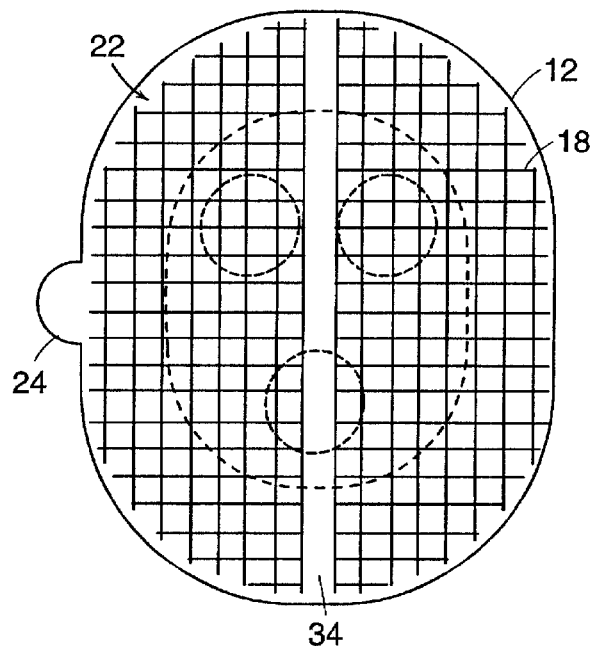
FIG. 7 illustrates a bottom view of a membrane for drug delivery device.

FIG. 7 shows a bottom view of the membrane 12 of the drug delivery device 10. The bottom surface 22 of the membrane 12 comprises, in a preferred embodiment, a surface attachment mechanism 34 and electrodes 18. In a preferred embodiment, the surface attachment mechanism 34 is an adhesive layer. The adhesive layer allows attachment of the drug delivery device 10 to a patient's skin.

In one embodiment, the electrodes 18 are printed on the membrane 12. In another embodiment, the electrodes 18 are printed on the bottom surface 20 of the membrane 12. The electrodes 18 can be printed in a grid pattern to provide for coverage of the surface area.

Figure 8:
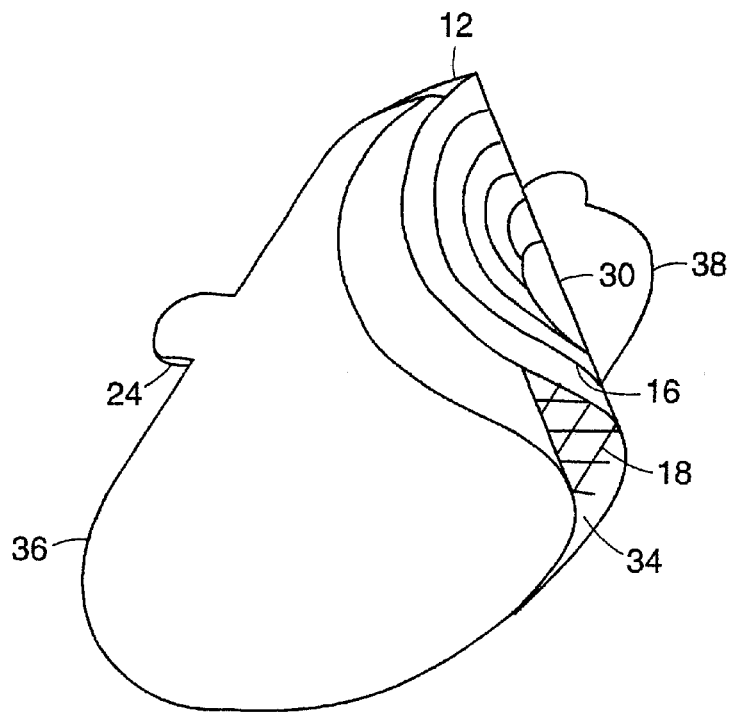
FIG. 8 shows a bottom perspective view of a membrane with both a top and bottom adhesive backing.

A bottom view of the drug delivery device 10 is depicted in FIG. 8. A bottom adhesive backing or cover 36 and a top adhesive backing 38 are shown. The adhesive backings 36, 38 protect the respective adhesive layers 30, 32, 34 of the membrane 12 prior to use of the drug delivery device 10.

Figure 9:
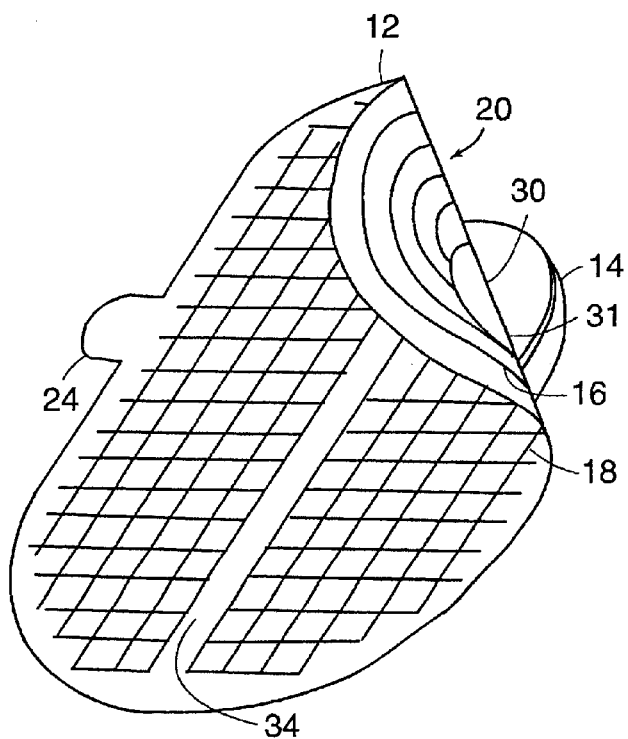
FIG. 9 illustrates a bottom perspective view of a drug delivery device including the attachment of the membrane to the control signal source.

FIG. 9 shows the attachment between the membrane 12 and the control signal source 14. The top surface 20 of the membrane 12 is attached to the control signal source 14 at two main areas. One area includes the interface between the membrane electrode contacts 31 and the housing electrode contacts 26 on the control signal source 14. The second area includes the interface between the antenna contact 33 and the housing antenna contact 28 on the control signal source 14.

Figure 10:
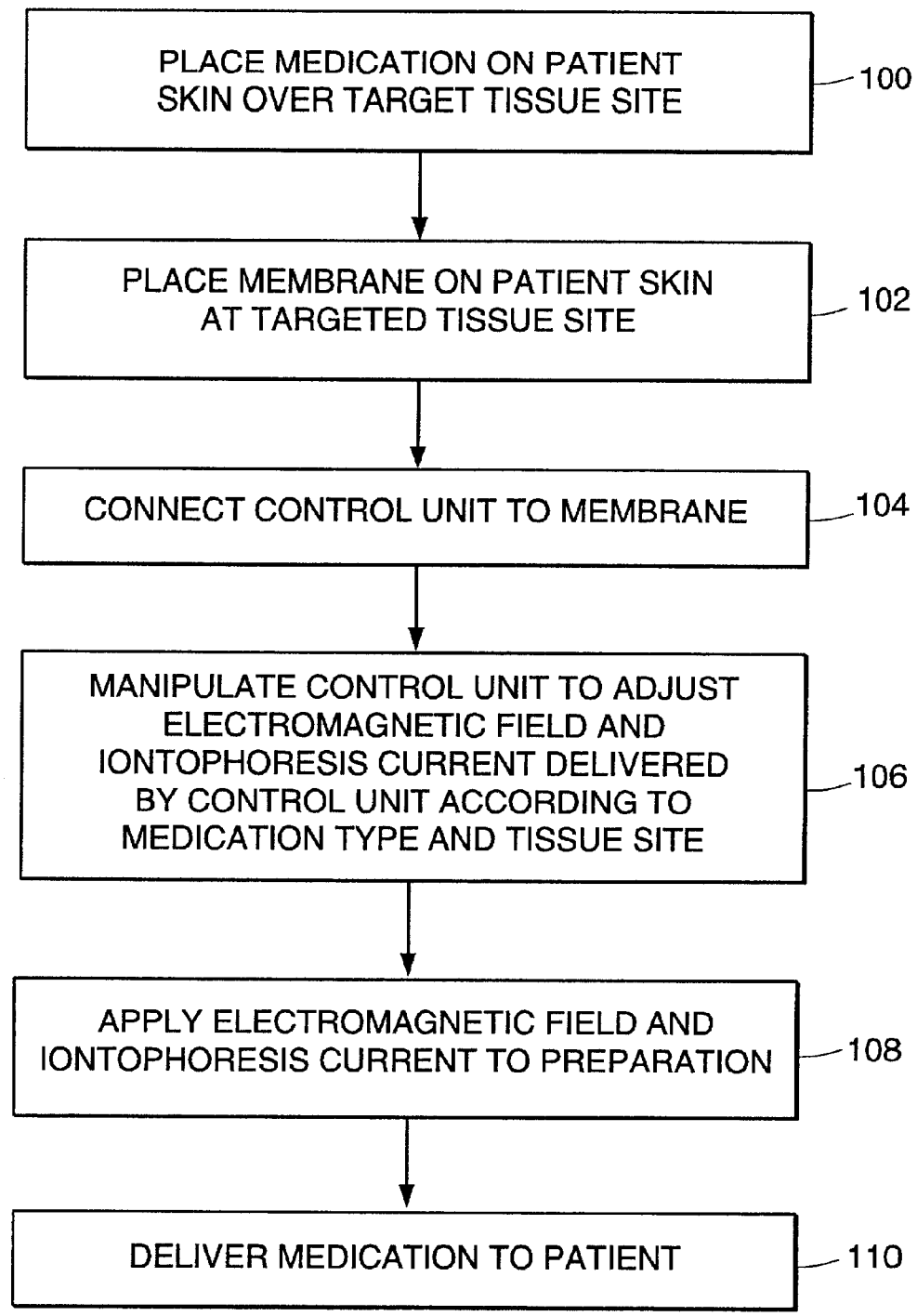
FIG. 10 shows a process flow chart outlining a method for using the drug delivery device.

FIG. 10 shows a process flow chart outlining a method for using the drug delivery device. First, the medical preparation to be delivered to a patient is placed on his skin over the targeted tissue site 100. In an alternate embodiment, this step may be bypassed when the drug delivery device includes a preparation as part of the delivery system. Next the membrane of the drug delivery device is placed oil the patient's skin at the targeted tissue site 102. The membrane is then connected to the control signal source 104. The user then selects the appropriate electromagnetic field and the current by adjusting the control signal source 106. The control signal source allows the user to select the field and current output of the drug delivery device to match the requirements needed by the various types of medication being delivered and the types of tissue being targeted. This process can be performed either manually in the control signal source or from an external computer either by physical interconnection between the control signal source and computer or by a wireless means between a receiver in the control signal source and a transmitter attached to a computer. With the electromagnetic field and the current levels chosen, the electromagnetic field is applied to the site and the current is applied to the preparation 108. Application of the field and the current to the site will cause delivery of the medical preparation to the patient 110. The current stimulates the iontophoretic process while the electromagnetic field stimulates the flow of blood in the area, thus enhancing the delivery of the medication.

Figure 11:
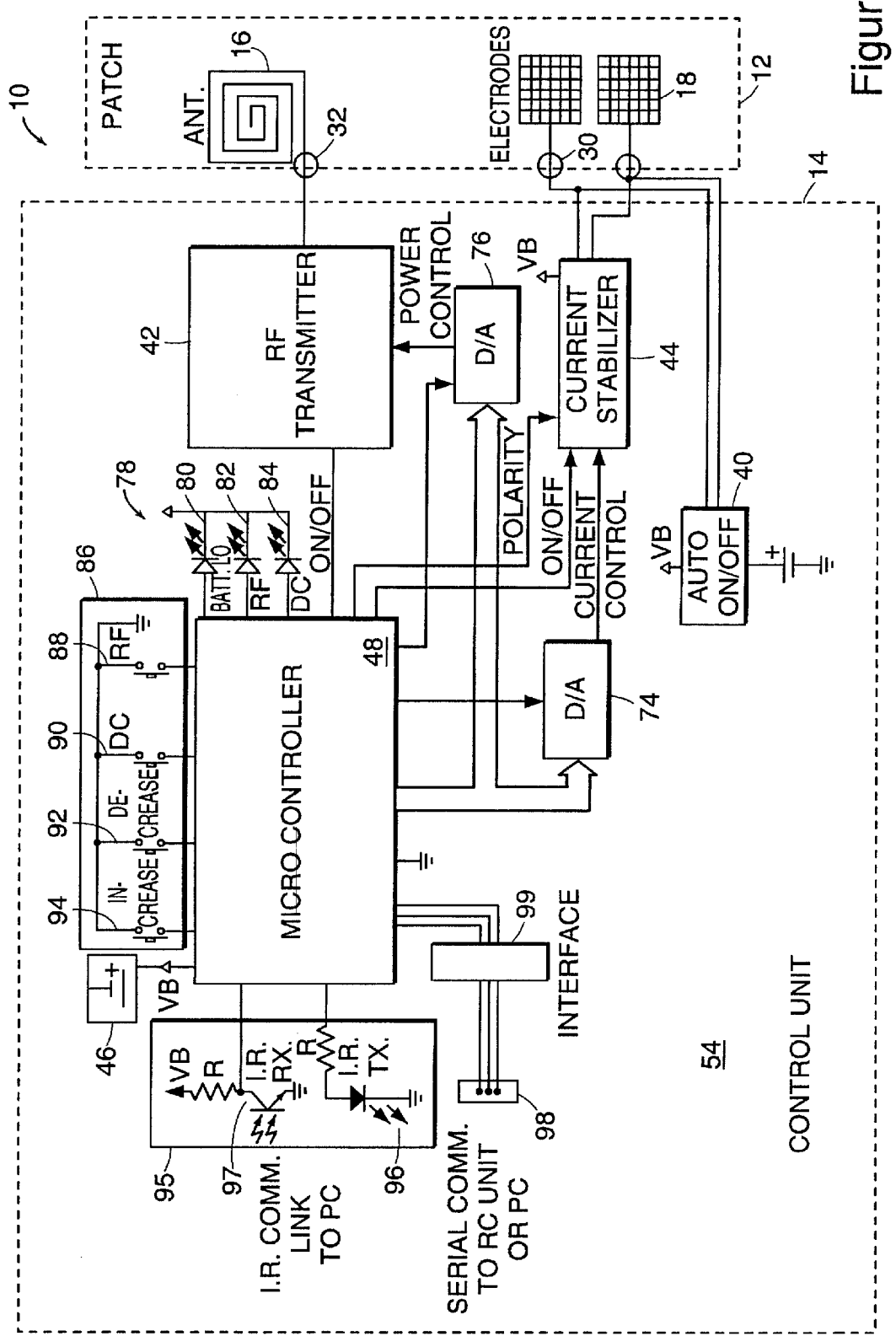
FIG. 11 shows a schematic representation of the drug delivery device.
Figure 12:
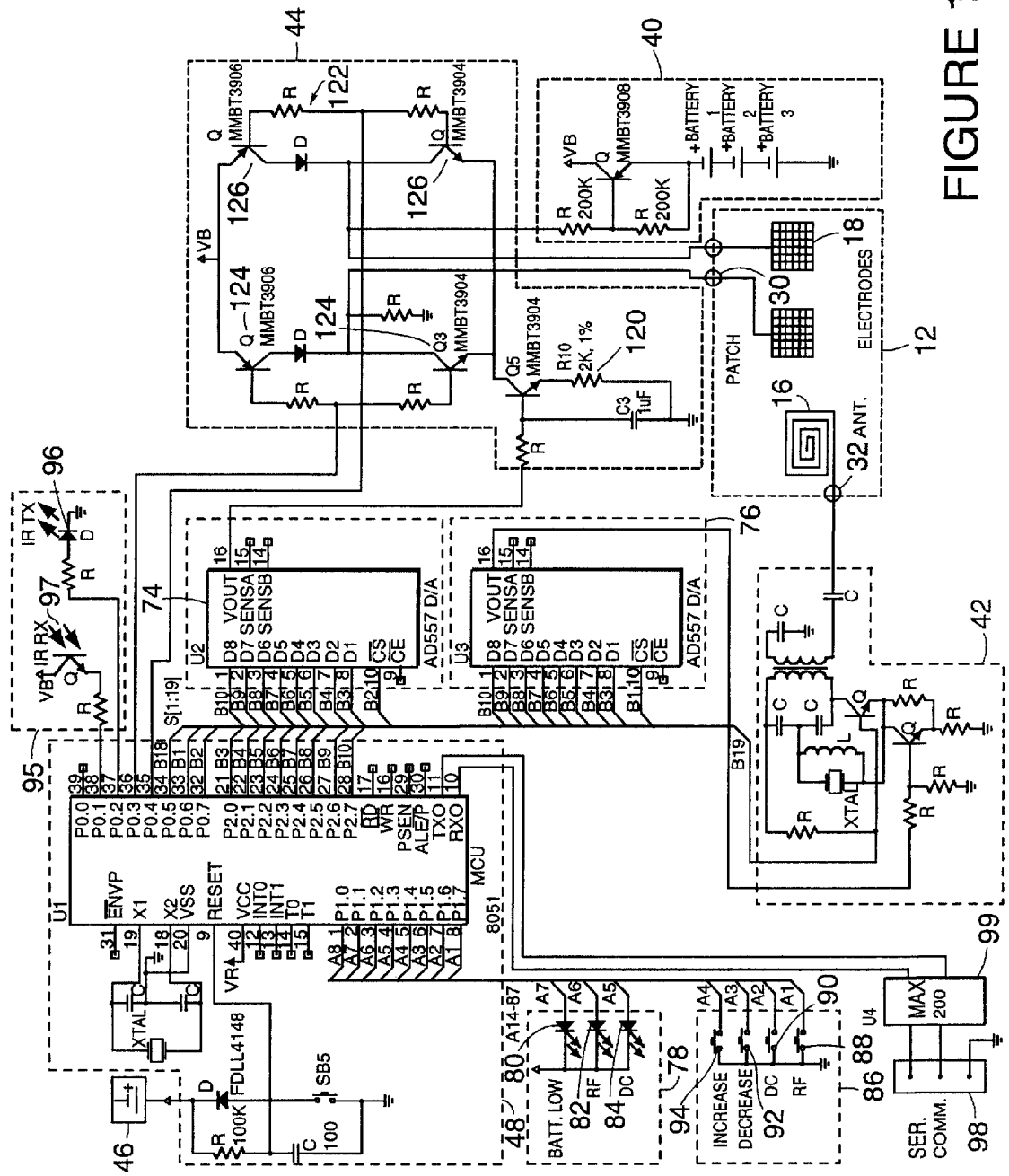
FIG. 12 shows a detailed schematic representation of the drug delivery device.

FIGS. 11 and 12 illustrate a schematic representation of a drug, delivery device 10. A control signal source 14 comprises, in this embodiment, a power source 46, a microprocessor 48, a first D/A (digital to analog) converter 74, a current stabilizer 44, a second D/A converter 76, an RF transmitter 42, and a current switch 40 all mounted on a single circuit board 54. The power source 46 provides power to the microprocessor 48, the RF transmitter 42, and the current stabilizer 44. In a preferred embodiment, the power source 46 is a battery. The microprocessor 48 provides current, by way of the first D/A converter 74 and second D/A converter 76 which convert a digital signal into a voltage, to both the current stabilizer 44 and RF transmitter 42, respectively. The current stabilizer 44 and RF transmitter 42 then transmit a current an electromagnetic field, respectively, to the membrane 12. The membrane comprises an antenna 16, a set of electrodes 18, an adhesive for the antenna contact 32, and adhesives for the electrode contacts 30. The control signal source 14 and the membrane 12 are separate elements connected by a conductive adhesive between the control signal source 14 and membrane antenna contacts 32 and the electrode contacts 30. The control signal source 14 is easily removed from the membrane 12 for reuse while the membrane 12 is disposed after a single use.

The control signal source 14 can contain a power indicator bay 78. In a preferred embodiment, the indicator bay 78 can contain a low power source indicator 80, an RF power indicator 82, and a DC power indicator 84. In one embodiment, the indicators 80, 82, and 84 are light sources. In another embodiment, the indicators 80, 82, and 84 are light emitting diodes.

The control signal source 14 can also contain a switch bay 86. In a preferred embodiment, the switch bay 86 contains an RF on-off switch 88, a DC on-off switch 90, an RF level control switch 92, and a DC level control switch 94. The RF on-off switch 88 and DC on-off switch 90 control the modes of operation, either on or off, of the RF transmitter 42 and current stabilizer 44 respectively. The RF level control switch 92 and DC level control switch 94 provide for an increase or a decrease in the amount of current produced or distributed by the RF transmitter 42 and current stabilizer 44, respectively. In one embodiment, the switches 88, 90, 92, and 94 are controlled manually. In an alternate embodiment, the switches 88, 90, 92, 94 are controlled electronically. Electronic control of the switches can originate from the microprocessor 48 or from an external source.

The control signal source 14 can also contain a communication port to allow a user to externally program the microprocessor 48. FIG. 11 illustrates a preferred embodiment of the invention, where the control signal source 14 contains a serial communication port 98 and a wireless communication port 95. The serial communication port 98 attaches to the microprocessor 48 by an interface 99 and allows wire connection between the microprocessor 48 and an external computer. External computer connection allows the user to externally adjust DC programmable variable and RF programmable variables. The wireless communication port 95 can comprise both a wireless transmitter 96 and a wireless receiver 97. The wireless communications port 95 allows a wireless connection between the microprocessor 48 and an external computer having a compatible transmitter and receiver. In a preferred embodiment, the transmitter 96 and receiver 97 comprise an infrared transmitter and receiver.

External computer connection allows the user to externally adjust DC programmable variable and RF programmable variables. In a preferred embodiment, the DC programmable variables include DC application (on/off), DC level, DC polarity, DC pulse shape, pulse width, DC pulse repetition rate, and total cycle time. The DC polarity selection can comprise a positive polarity, a negative polarity, or an alternating polarity. The DC pulse shape can be programmed as a square, triangle or sawtooth wave. In an additional embodiment, the DC pulse repetition rate is continuous but can be adjusted for various treatments. In another preferred embodiment, the RF programmable variables include RF application (on/off), RF amplitude, RF pulse shape, pulse width, RF pulse repetition rate, and total cycle time. The RF pulse shape can be programmed as a square wave, or alternatively, as a triangle or sawtooth wave. The RF pulse repetition rate can be continuous with different repetition rates for various treatments.

The external computer connection can also allow the user to program combined DC and RF cycles in any sequence or total cycle time. The DC and RF cycles can be programed to operate in combination either simultaneously or alternately. The DC and RF cycles can also be programed to operate independent of each other. A user can thus program the microprocessor to apply either DC cycles or RF cycles exclusively to a site.

The DC and RF programmable variables, as outlined, can be programmed by the user, in an alternate embodiment, on the control signal source 14 itself. The sequence of combinations or independence of the DC and RF cycles can similarly be programmed on the control signal source 14 itself in the alternate embodiment.

The current stabilizer 44, as shown in FIG. 12 contains a current control circuit 120 and a polarity circuit 122. In a preferred embodiment a voltage is carried into the current stabilizer 44 through a D/A converter 74. The voltage travels through the current control circuit 120, the purpose of which is to provide a constant voltage DC current to the electrodes 18. The current control circuit 120 prevents any fluctuations in the current from reaching the electrodes 18. The stabilized current, in this embodiment, travels to the polarity circuit 122 in the current stabilizer 44.

The polarity circuit 122 forces the current to exit the current stabilizer with either a positive or a negative polarity. Polarity is determined by the direction of travel of the current through the polarity circuit. The microprocessor 45 controls the direction of travel of the current through the circuit by means of a first second set of switches 124, 126. When the first set of switches 124 is closed and the second set of switches 126 is opened, the current travels in a counterclockwise direction creating a first polarity. When the first set 124 is opened and the second set 125 is closed, the current travels in a clockwise direction creating an opposite polarity.

The current switch 40, in a preferred embodiment, is a control feedback switch. The current switch 40 detects when the electrodes 18 of the membrane 12 have been disconnected from a patient. When there is no contact between the electrodes and the patient, the current switch 40 turns the current stabilizer 44 to an "off" mode of operation.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A drug delivery device comprising:
    a membrane;
    an antenna mounted to the membrane that emits an electromagnetic field onto a treatment site, the electromagnetic field having a frequency and intensity that alters a condition at the treatment site;

an electrode mounted to the membrane that provides a current through the membrane; and a circuit that connects a control signal source to the antenna and the electrode, the signal source activating emission of the electromagnetic field and the electrode current.

2. The drug delivery device of claim 1 wherein the device further comprises an iontophorectic preparation.

3. The drug delivery device of claim 2 wherein the iontophoretic preparation comprises a preparation layer attached to the membrane.

4. The drug delivery device of claim 2 wherein the iontophoretic preparation comprises a reservoir attached to the membrane.

5. The drug delivery device of claim 1 wherein the membrane comprises a flexible material.

6. The drug delivery device of claim 5 wherein the flexible material comprises paper.

7. The drug delivery device of claim 1 wherein the membrane comprises a material having a thickness in the range of 0.1 mm and 0.5 mm.

8. The drug delivery device of claim 1 wherein the membrane has a surface area in the range of 5 $cm^2$ to 200 $cm^2$.

9. The drug delivery device of claim 1 wherein the membrane further comprises a surface attachment device.

10. The drug delivery device of claim 9 wherein the surface attachment device comprises an adhesive layer on a bottom surface of the membrane.

11. The drug delivery device of claim 1 wherein the membrane further comprises a plurality of electronically conductive adhesive areas on the top surface for electrical and mechanical contact with the control signal source.

12. The drug delivery device of claim 1 wherein the antenna is printed onto the membrane.

13. The drug delivery device of claim 12 wherein the antenna is printed onto a top surface of the membrane.

14. The drug delivery device of claim 1 wherein the electromagnetic field comprises a radio frequency signal.

15. The drug delivery device of claim 13 wherein the radio frequency signal is in the range of 10 MHZ to 3 GHz.

16. The drug delivery device of claim 14 wherein the radio frequency signal is pulsed with a duty cycle.

17. The drug delivery device of claim 14 wherein the radio frequency (RF) signal has an RF power in the range of 10 mW and 1 W.

18. The drug delivery device of claim 10 wherein the antenna is less than 1 mm from the bottom surface.

19. The drug delivery device of claim 1 wherein the electrode comprises a plurality of electrodes printed onto the membrane.

20. The drug delivery device of claim 19 wherein the plurality of electrodes have been printed onto the membrane.

21. The drug delivery device of claim 1 wherein the current comprises a current in the range of 50 uA and 4 mA.

22. The drug delivery device of claim 1 wherein the current is pulsed by the control signal source in synchrony with electromagnetic pulses from the antenna.

23. The drug delivery device of claim 1 wherein the control signal source further comprises a battery.

24. The drug delivery device of claim 1 wherein the control signal source simultaneously transmits the electromagnetic field with the current.

25. The drug delivery device of claim 1 wherein the control signal source alternately actuates transmission of the electromagnetic field or the current.

26. The drug delivery device of claim 1 wherein the control signal source selectively transmits either the electromagnetic field or the current.

27. The drug delivery device of claim 1 wherein the control signal source further comprises a current switch.

28. The drug delivery device of claim 27 wherein the current switch stops the current when the drug delivery device is removed from a surface.

29. The drug delivery device of claim 1 wherein the control signal source further comprises a microprocessor.

30. The drug delivery device of claim 29 wherein the control signal source further comprises an input port for connection between the microprocessor and an external programming source.

31. The drug delivery device of claim 29 wherein the control signal source further comprises a wireless receiver for wireless connection between the microprocessor and an external programming source.

32. The drug delivery device of claim 29 wherein the control signal source further comprises plurality of switches to access programs in the microprocessor.

33. The drug delivery device of claim 1 further comprising a display that is connected to the control signal source.

34. A method of delivering a preparation to a patient comprising:

attaching a membrane to a skin surface of a patient in a region of interest, the membrane comprising an antenna for transmitting an electromagnetic field and an of electrode that transmits a current;

connecting the antenna and electrode to a control signal source;

activating the control signal source;

applying the electromagnetic field to the region of interest and applying the current to a preparation; and delivering the preparation to the region of interest.

35. The method of claim 34 further comprising providing the preparation to an area of skin of the patient prior to attaching the membrane.

36. The method of claim 34 wherein the step of applying the electromagnetic field comprises generating a sequence of radio frequency (RF) pulses.

37. The method of claim 34 further comprising attaching the patch to the area of skin with an adhesive.

38. A method of delivering a preparation to a patient comprising:

attaching a membrane comprising an antenna for transmitting an electromagnitic field, an electrode that conducts a current, and a preparation on and area of skin of a patient;

connecting the antenna and electrodes to a control signal source;

activating the control signal source;

applying the electromagnetic field to the area and the current to the preparation; and moving the preparation through the skin of the patient.

39. The method of claim 38 wherein the applying step comprises generating a radio frequency (RF) signal with the antenna and simultaneously delivering current across the plurality of electrodes.

40. The method of claim 38 further comprising alternating application of the electromagnetic field and the current.

41. The method of claim 38 further comprising providing a phase shift between radio frequency (RF) pulses and current pulses.

42. The method of claim 38 further comprising providing a working electrode and a counterelectrode.

43. The method of claim 38 further comprising varying a duty cycle of a radio frequency (RF) signal transmitted by the antenna.

44. The method of claim 38 further comprising attaching the membrane to the skin with an adhesive layer.

45. The method of claim 44 further comprising a second adhesive layer that attaches the membrane to a controller housing.

46. A method of enhancing the delivery of and agent across skin comprising the steps of:
  attaching a membrane to a patient's skin surface, the membrane having an antenna and an electrode in electrical communication with an agent to be delivered through the skin surface; and
  concurrently applying an electromagnetic field at the skin surface and a an electrical current to the skin surface.

47. The method of claim 46 further comprising attaching a circuit housing to the membrane, the membrane having electrical contacts that electrically connect the antenna and the electrode to the circuit housing.

48. The method of claim 47 wherein the circuit housing has a control panel, a processor and a battery.

* * * * *